United States Patent
Kim et al.

(10) Patent No.: US 9,033,505 B2
(45) Date of Patent: May 19, 2015

(54) METHOD OF TRACKING A POSITION OF AN EYE AND A MEDICAL HEAD LAMP USING THE SAME

(75) Inventors: Sung Min Kim, Gyeonggi-do (KR); Sang Hoon Hong, Gyeonggi-do (KR); Chan Beom Jeong, Gyeonggi-do (KR); Jeon Pil Han, Seoul (KR); Kwon Hee Lee, Gyeonggi-do (KR)

(73) Assignee: Dongguk University Industry-Academic Cooperation Foundation (KR)

( * ) Notice: Subject to any disclaimer, the term of this patent is extended or adjusted under 35 U.S.C. 154(b) by 34 days.

(21) Appl. No.: 13/515,581

(22) PCT Filed: Jan. 31, 2012

(86) PCT No.: PCT/KR2012/000711
§ 371 (c)(1),
(2), (4) Date: Jun. 12, 2013

(87) PCT Pub. No.: WO2012/124893
PCT Pub. Date: Sep. 20, 2012

(65) Prior Publication Data
US 2014/0039273 A1    Feb. 6, 2014

(30) Foreign Application Priority Data
Mar. 15, 2011    (KR) .......... 10-2011-0022856

(51) Int. Cl.
*A61B 3/10*    (2006.01)
*F21V 21/084*    (2006.01)
(Continued)

(52) U.S. Cl.
CPC . *A61B 1/06* (2013.01); *A61B 3/111* (2013.01); *A61B 3/113* (2013.01);
(Continued)

(58) Field of Classification Search
CPC . G06K 9/0061; G06K 9/00604; A61B 3/111; F21V 21/084
USPC ........... 382/105, 106, 117; 362/105, 106, 804
See application file for complete search history.

(56) References Cited

U.S. PATENT DOCUMENTS 5,357,293 A * 10/1994 Uomori et al. ................ 351/209
5,382,989 A *  1/1995 Uomori et al. ................ 351/209
(Continued)

FOREIGN PATENT DOCUMENTS

JP    2002/324403    11/2002
JP    2003/036704     2/2003
(Continued)

OTHER PUBLICATIONS

Official Action prepared by the United States Patent and Trademark Office for U.S. Appl. No. 13/515,766, mailed Oct. 22, 2013, 13 pages.

*Primary Examiner* — Eduardo C Robert
*Assistant Examiner* — Stuart S Bray
(74) *Attorney, Agent, or Firm* — Swanson & Bratschun, L.L.C.

(57) ABSTRACT

A method of tracking a position of an eye is provided. The method of tracking a position of an eye includes converting an obtained image into a binary number image, classifying the corner of the eye, maximum and minimum values of a pupil of the eye, and extracting a feature point from the binary number image on which the binarization step is completed, calculating a distance and inclination between the corner and the pupil of the eye using the feature point extracted through the feature point extraction step, and determining a gaze direction of the eye based on the distance and inclination calculated through the distance and inclination calculation step.

7 Claims, 3 Drawing Sheets

(51) Int. Cl.
*A61B 1/06* (2006.01)
*A61B 3/11* (2006.01)
*A61B 3/113* (2006.01)
*A61B 19/00* (2006.01)
*G06K 9/00* (2006.01)
*G02B 27/00* (2006.01)
*G06T 7/00* (2006.01)
*G06T 7/20* (2006.01)
*F21V 21/14* (2006.01)
*A61B 17/00* (2006.01)

(52) U.S. Cl.
CPC .......... *A61B 19/5202* (2013.01); *F21V 21/084* (2013.01); *F21V 21/145* (2013.01); *A61B 2019/262* (2013.01); *G06K 9/0061* (2013.01); *A61B 2017/00216* (2013.01); *G02B 27/0093* (2013.01); *G06T 7/0042* (2013.01); *G06T 7/2033* (2013.01); *G06T 2207/30201* (2013.01); *G06K 9/00604* (2013.01)

(56) References Cited

U.S. PATENT DOCUMENTS

| | | | |
|---|---|---|---|
| 5,975,703 A * | 11/1999 | Holman et al. | 353/20 |
| 6,585,724 B2 * | 7/2003 | Toh | 606/5 |
| 6,608,615 B1 * | 8/2003 | Martins | 345/156 |
| 6,690,451 B1 * | 2/2004 | Schubert | 356/3.14 |
| 7,321,385 B2 * | 1/2008 | Rus et al. | 348/69 |
| 7,362,883 B2 * | 4/2008 | Otsuka et al. | 382/104 |
| 7,370,991 B1 * | 5/2008 | Ellis-Fant | 362/233 |
| 7,379,567 B2 * | 5/2008 | Azuma et al. | 382/117 |
| 7,416,301 B2 * | 8/2008 | Hanebuchi et al. | 351/205 |
| 7,524,064 B2 * | 4/2009 | Wyatt | 351/211 |
| 7,796,784 B2 * | 9/2010 | Kondo et al. | 382/117 |
| 7,815,342 B2 * | 10/2010 | Medinis | 362/294 |
| 7,862,172 B2 * | 1/2011 | Yoshinaga et al. | 351/210 |
| 8,175,331 B2 * | 5/2012 | Nagaoka et al. | 382/103 |
| 8,175,337 B2 * | 5/2012 | Park et al. | 382/106 |
| 8,500,278 B2 * | 8/2013 | Lo et al. | 351/206 |
| 8,652,044 B2 * | 2/2014 | Abramov | 600/401 |
| 8,678,589 B2 * | 3/2014 | Sakata et al. | 351/209 |
| 2001/0021108 A1 * | 9/2001 | Shimada et al. | 362/103 |
| 2002/0063851 A1 * | 5/2002 | Shibutani et al. | 351/210 |
| 2002/0085372 A1 * | 7/2002 | Lehrer | 362/105 |
| 2005/0013488 A1 * | 1/2005 | Hashimoto et al. | 382/216 |
| 2005/0152583 A1 * | 7/2005 | Kondo et al. | 382/117 |
| 2006/0120570 A1 * | 6/2006 | Azuma et al. | 382/117 |
| 2007/0100327 A1 * | 5/2007 | Smith | 606/4 |
| 2010/0110374 A1 * | 5/2010 | Raguin et al. | 351/206 |
| 2011/0206135 A1 * | 8/2011 | Drugeon et al. | 375/240.24 |
| 2011/0299742 A1 * | 12/2011 | D'Hose | 382/117 |
| 2012/0045099 A1 * | 2/2012 | Ishioka | 382/106 |
| 2012/0120635 A1 * | 5/2012 | Strong et al. | 362/105 |
| 2012/0140989 A1 * | 6/2012 | Hori | 382/106 |
| 2012/0147328 A1 * | 6/2012 | Yahav | 351/210 |
| 2012/0219180 A1 * | 8/2012 | Mehra | 382/103 |
| 2012/0275140 A1 * | 11/2012 | Feinbloom et al. | 362/105 |
| 2012/0294478 A1 * | 11/2012 | Publicover et al. | 382/103 |
| 2012/0328150 A1 * | 12/2012 | Pelz et al. | 382/103 |
| 2013/0010096 A1 * | 1/2013 | S. et al. | 348/78 |
| 2013/0016102 A1 * | 1/2013 | Look et al. | 345/426 |
| 2013/0114850 A1 * | 5/2013 | Publicover et al. | 382/103 |
| 2013/0170754 A1 * | 7/2013 | Tsukizawa et al. | 382/195 |
| 2013/0178287 A1 * | 7/2013 | Yahav | 463/32 |
| 2013/0194408 A1 * | 8/2013 | Hanna et al. | 348/78 |
| 2013/0294659 A1 * | 11/2013 | Hanna et al. | 382/117 |
| 2013/0322053 A1 * | 12/2013 | Kim et al. | 362/33 |
| 2014/0072183 A1 * | 3/2014 | Hanna et al. | 382/117 |

FOREIGN PATENT DOCUMENTS

| | | |
|---|---|---|
| JP | 2006-209442 | 8/2006 |
| JP | 2010-230651 | 10/2010 |
| KR | 2000-0060570 | 10/2000 |
| KR | 2006/0131775 | 12/2006 |
| KR | 2008/0086143 | 9/2008 |
| KR | 2010-0119420 | 11/2010 |

* cited by examiner

METHOD OF TRACKING A POSITION OF AN EYE AND A MEDICAL HEAD LAMP USING THE SAME

CROSS-REFERENCE TO RELATED APPLICATION

This application is a 35 U.S.C. §371 national phase application of PCT/KR2012/000711, filed on Jan. 31, 2012, entitled "METHOD OF TRACKING A POSITION OF AN EYE AND A MEDICAL HEAD LAMP USING THE SAME", which application claims priority to and the benefit of Korean Patent Application No. 2011-0022856, filed Mar. 15, 2011, the disclosure of which is incorporated herein by reference in its entirety.

BACKGROUND

1. Field of the Invention

The present invention relates to a method of tracking a position of an eye and a medical head lamp using the same, and more particularly, to a method of tracking a position of an eye which is able to illuminate a dark diseased part or a desired part by adjusting a lighting direction of a lamp based on positions of the physician's eyes without the direct manual operation of a head lamp when the physician medically examines and treats a patient, and a medical head lamp using the same.

2. Discussion of Related Art

Generally, a head lamp has been used in the fields of mining, medicine, and particularly surgery. Typically, the head lamp is attached to a head band, a hat or a helmet.

Such a head lamp has an advantage in that a region at which a user wearing the head lamp looks can be illuminated without using a fixed floodlight or a portable lamp.

In particular, when the head lamp is used for medical service, that is, when a physician observes and operates on a diseased part, a desired part is brightly illuminated so that the medical procedure can be practiced more easily.

However, the medical head lamp is fixed on the head regardless of the direction of the physician's gaze. Therefore, when a position of the head lamp has to be adjusted during surgery, a nurse rather than an operating physician manually adjusts the direction of the head lamp worn on the head of the physician so as to prevent the patient from being contaminated.

Here, when the physician adjusts the head lamp mounted on his head himself, it is possible to place the head lamp at a desired position of the head more quickly and accurately, but surgical tools such as surgical gloves may be contaminated.

SUMMARY OF THE INVENTION

The present invention is directed to providing a method of tracking a position of an eye. Here, the method includes binarizing an image of a region of an eye taken by an imaging unit and extracting a feature point from the image.

Also, the present invention is directed to providing a medical head lamp which uses an imaging unit to image a physician's eye, calculates a position of the eye from an obtained image using the method of tracking a position of an eye, and enables a lighting direction of a head lamp to automatically correspond to the direction of the physician's gaze based on the calculated position of the eye.

One aspect of the present invention provides a method of tracking a position of an eye, which includes:

i) a binarization step to convert an obtained image into a binary number image;

ii) a feature point extraction step to classify the corner of the eye, maximum and minimum values of the pupil of the eye and extract a feature point from the binary number image on which the binarization step is completed;

iii) a distance and inclination calculation step to calculate a distance and inclination between the corner and the pupil of the eye using the feature point extracted through the feature point extraction step; and iv) an eye gaze direction determination step to determine a gaze direction of the eye based on the distance and inclination calculated through the distance and inclination calculation step.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Figure 1:
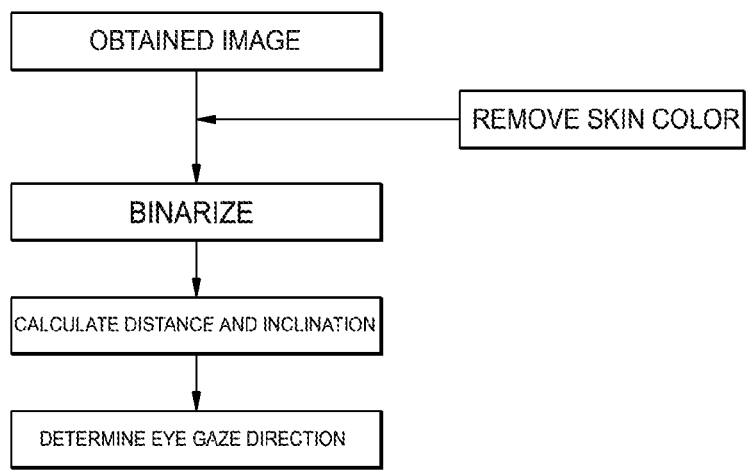
FIG. 1 is a flowchart showing a method of tracking a position of an eye according to the present invention.

Hereinafter, the exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and similarly, a second element could be termed a first element, without departing from the scope of the exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of the exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, the exemplary embodiments of the present invention will be described in detail below. To aid in understanding the present invention, like numbers refer to like elements throughout the description of the figures, and the description of the same elements will not be reiterated.

According to one aspect, the present invention provides a method of tracking a position of an eye, which includes i) a binarization step to convert an obtained image into a binary number image; ii) a feature point extraction step to classify the corner of the eye, maximum and minimum values of the pupil of the eye and extract a feature point from the binary number image on which the binarization step is completed; iii) a distance and inclination calculation step to calculate a distance and inclination between the corner and the pupil of the eye using the feature point extracted through the feature point extraction step; and iv) an eye gaze direction determination step of determining a gaze direction of the eye based on the distance and inclination calculated through the distance and inclination calculation step.

According to another aspect, the present invention provides a medical head lamp capable of controlling a lighting direction of the medical head lamp using the method of tracking a position of an eye.

In particular, the medical head lamp uses an imaging unit to take an image of a physician's eye, calculates a position of the eye from the obtained image using the method of tracking a position of an eye, and enables the lighting direction of the head lamp to automatically correspond to the direction of the physician's gaze based on the calculated position of the eye.

Here, the medical head lamp functions to automatically illuminate a dark diseased part or a desired part based on positions of the physician's eyes, preferably, positions of the pupils of the eyes without the direct manual operation of a head lamp when the physician medically examines and treats a patient. Therefore, head lamps may be used without limitation as long as they are used for this purpose.

In particular, the head lamp according to the present invention may apply to medical services and applications in which a user wants to wear the head lamp on the head and illuminate a desired position based on the direction of the user's gaze, for example, repair work, mining, etc.

Hereinafter, the present invention will be described in further detail with reference to the accompanying drawings. However, it should be understood that the description below pertains merely to a preferable example for the purpose of illustration only and is not intended to limit the scope of the invention.

Figure 2:
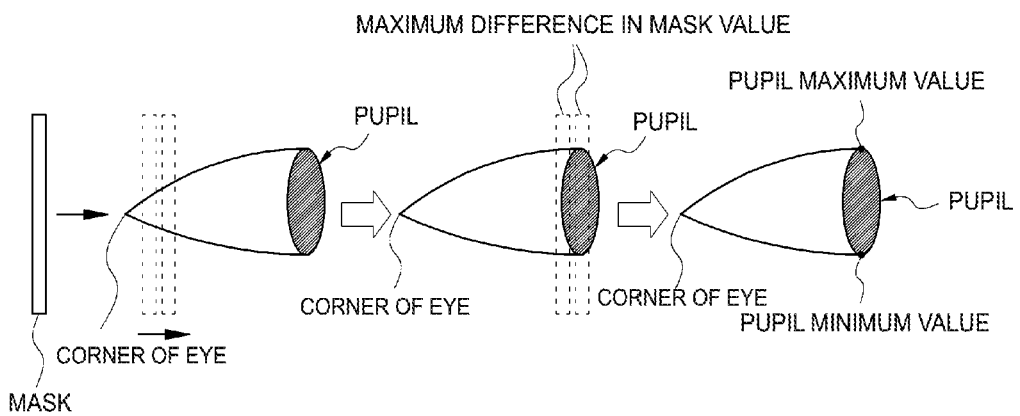
FIG. 2 is a diagram showing the extraction of a feature point of an eye according to the present invention.
Figure 3:
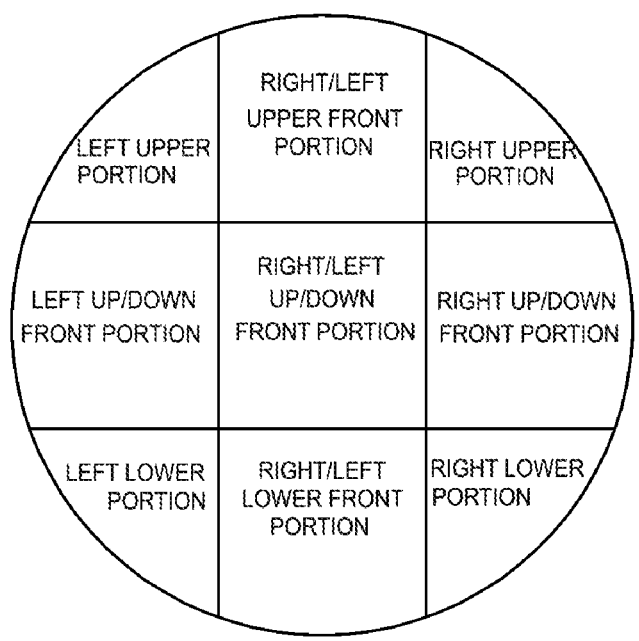
FIG. 3 is a diagram showing a gaze direction of an eye according to the present invention.
Figure 4:
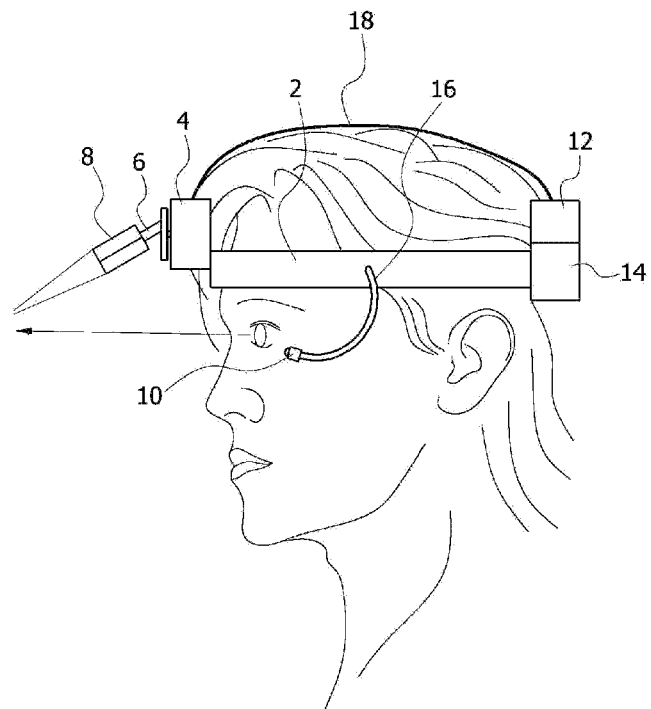
FIG. 4 is a configuration diagram showing a medical head lamp according to the present invention.
Figure 5:
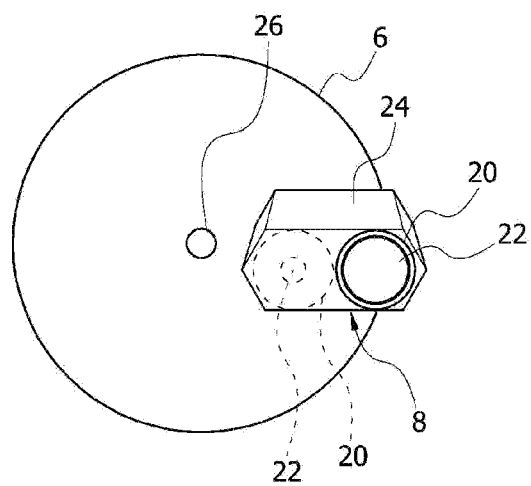
FIG. 5 is a configuration diagram showing a lamp unit and a position adjustment unit of the medical head lamp according to the present invention.

FIG. 1 is a flowchart showing a method of tracking a position of an eye according to the present invention, FIG. 2 is a diagram showing the extraction of a feature point of an eye according to the present invention, FIG. 3 is a diagram showing the gaze direction of an eye according to the present invention, FIG. 4 is a configuration diagram showing a medical head lamp according to the present invention, and FIG. 5 is a configuration diagram showing a lamp unit and a position adjustment unit of the medical head lamp according to the present invention.

As shown in FIGS. 1 to 5, the method of tracking a position of an eye according to the present invention includes i) a binarization step to convert an obtained image into a binary number image; ii) a feature point extraction step to classify the corner of the eye, maximum and minimum values of the pupil of the eye and extract a feature point from the binary number image on which the binarization step is completed; iii) a distance and inclination calculation step to calculate a distance and inclination between the corner and the pupil of the eye using the feature point extracted through the feature point extraction step; and iv) an eye gaze direction determination step of determining a gaze direction of the eye based on the distance and inclination calculated through the distance and inclination calculation step.

The binarization step of Step i) according to the present invention is performed to convert an obtained image into a binary number image. Here, binarization methods may be used without limitation as long as they are used for this purpose.

In particular, the binarization step includes dividing an obtained image, preferably an image of an obtained eye region, into partitions and converting the image pixels in each of the partitions into binary numbers, for example, "0" or "1," based on a predetermined critical value.

Here, the critical value may vary according to the user's choice. Upon binarization of the image pixels, the binary numbers "0" and "1" may also be reversely set based on the critical value, depending on the user's choice.

Also, the obtained image is an image taken of a region an eye positioned on the face. In this case, the image may be an image taken of each of left/right eye regions, and includes both a black/white image and a color image.

In this case, each of the obtained images of the left/right eye regions may sequentially undergo the binarization step, the feature point extraction step, and the distance and inclination calculation step to track a position of the eye.

In particular, prior to the binarization step according to the present invention, the method of tracking a position of an eye according to the present invention may further include a skin color removal operation to remove skin color from the obtained image.

In this case, the obtained image used for the skin color removal operation may be a color image.

Also, the removal of the skin color may be performed by binarizing the obtained image only when red, green and blue pixel values in the image satisfy a predetermined range.

In this case, for example, the set pixel values are in the range of 50 to 100 for red pixels, in the range of 20 to 50 for green pixels, and in the range of 200 to 255 for blue pixels. On the assumption that the pixel values are binarized, when the range values are all satisfied, the corresponding region is a region corresponding to the white of the eye, and thus a binarized value may be set to "0," and when the range values are not satisfied, the corresponding region is a region corresponding to the contour of the eye, and thus a binarized value may be set to "1."

The feature point extraction step of Step ii) according to the present invention is performed by classifying the corner of the eye, maximum and minimum values of the pupil of the eye, and extracting a feature point from the binary number image on which the binarization step of Step ii) is completed. Here, typical methods may be used without limitation as long as they are used for these purposes.

Here, the corner of the eye refers to a lateral palpebral commissure of the eye.

In particular, the feature point extraction step includes translocating a mask from one end to another end of the binarized image with an increase of one pixel, storing a summation value at each pixel position upon the translocation, regarding a position in a region in which the summation value first becomes significant, that is, in which the contour of the eye is found for the first time, for example, in which a summation value is 3 or more, as the corner of the eye, regarding a position in which the difference between mask values summated at regular distances is greatest as a pupil region, and searching for the maximum and minimum values at a position of the pupil, as shown in FIG. 2.

Here, the mask means a region used to search a portion of the entire image, and the summation means the sum of the binarized values in the searched region. Also, the maximum value measured through the summation mask refers to the highest contour point of a pupil region, and the minimum value refers to the lowest contour point of the pupil region.

The distance and inclination calculation step of Step iii) according to the present invention is performed by calculating a distance and inclination between the corner and the pupil of the eye using the feature point extracted through the feature point extraction step of Step ii).

In addition, the positions of the corner and pupil of the eye are extracted through the feature point extraction step of Step ii). Here, the distance and inclination between the corner and pupil of the eye are calculated according to the following Equations 1 and 2.

Distance=(maximum value of pupil+minimum value of pupil)/2−corner of the eye    Equation 1

Inclination=maximum value of pupil−minimum value of pupil    Equation 2

Here, the maximum and minimum values of the pupil of the eye and the corner of the eye defined in Equations 1 and 2 refer to the pixel positions of a binarized image.

In particular, the maximum value of the pupil refers to the highest contour point of a pupil region, the minimum value of the pupil refers to the lowest contour point of the pupil region, and the corner of the eye refers to a position value of a region in which the contour of the eye is found.

The eye gaze direction determination step according to the present invention is performed by determining a gaze direction of the eye, based on the distance and inclination calculated through the distance and inclination calculation step of Step iv). Typical determination methods may be used without limitation as long as they are used for this purpose.

As one example of the eye gaze direction determination method, when the difference between a distance of a right eye and a distance of a left eye is higher than a threshold, the eye gaze is directed to the left, when the difference between the distance of the left eye and the distance of the right eye is higher than the critical point, the eye gaze is directed to the right, and when the difference does not meet the requirements, the eye gaze is directed to the left/right center, as shown in FIG. 3.

Also, when the average of an inclination of the right eye and an inclination of the left eye is higher than an upward critical point, the eye gaze is directed upward, when the average of an inclination of the left eye and the inclination of the right eye is lower than a downward threshold, the eye gaze is directed downward, and when the difference does not meet these requirements, the eye gaze is directed at up-down center.

Here, the threshold is an experimentally calculated value that may be set in advance according to the user's choice.

Meanwhile, the above-described method of tracking a position of an eye according to the present invention is applicable to all fields in which it is necessary to track a position of the eye.

Here, the medical head lamp includes a body 2 mounted on the head, a driving unit 4 coupled to one side of the body 2 to provide a driving force, a position adjustment unit 6 coupled to one side of the driving unit 4, a lamp unit 8 which is coupled to one side of the position adjustment unit 6, moves in response to the movement of the position adjustment unit 6, and emits light forward, an imaging unit 10 coupled to one side of the body 2 to take an image of an eye region, a controller 12 coupled to the driving unit 4 and the imaging unit 10 to analyze the image taken by the imaging unit 10, preferably calculate a position of the eye using the method of tracking a position of an eye according to the present invention, and activate the driving unit 4 based on the calculated position of the eye, and a power supply unit 14 coupled to the controller 12, the driving unit 4 and the lamp unit 8 to apply an electric current thereto.

The body 2 is mounted on a human's head. Here, typical devices known in the art may be used without particular limitation as long as they are used for this purpose.

A hair band, head band and the like may be used as the body 2.

The driving unit 4 is coupled to one side of the body 2, and more particularly, to one side of the body 2 that the direction of the human's gaze reaches, to provide a driving force to activate the position adjustment unit 6 coupled to the lamp unit 8 configured to emit light.

In this case, typical devices may be used without limitation as long as they function to provide a driving force. In this case, a motor may be used as the driving unit 4.

The adjustment unit 6 is coupled to one side of the driving unit 4, moves in response to the activation of the driving unit 4, and adjusts a position of the lamp unit 8.

Also, the lamp unit 8 is coupled to one side of the position adjustment unit 6 so that the position adjustment unit 6 can adjust a position of the lamp unit 8 in response to the activation of the driving unit 4.

Meanwhile, in order to automatically adjust a position of the lamp unit 8, a driving unit configured to translocate the lamp unit 8 to an x-coordinate and a driving unit configured to translocate the lamp unit 8 to a y-coordinate should be provided separately. However, the position adjustment unit 6 according to the present invention may adjust a position of the lamp unit 8 using one driving unit 4.

For this purpose, the position adjustment unit 6 according to the present invention functions to rotate the position adjustment unit 6 upon driving of the driving unit 4 to adjust a position of the lamp unit 8 since a driving shaft of the driving unit 4, for example, a rotational shaft of a motor, is positioned at the center of gravity 26 of the position adjustment unit 6, and the lamp unit 8 is coupled to one side of the position adjustment unit 6 and spaced a predetermined distance apart from the center of gravity 26 of the position adjustment unit 6 coupled to the driving shaft.

In this case, there is no limitation on the shape of the position adjustment unit 6 as long as the position adjustment unit 6 is coupled to the driving shaft of the driving unit 4. Preferably, the shape of the position adjustment unit 6 may be that of a plate, and more preferably, a plate extending in a radial direction, a circular plate, or a plate extending in a longitudinal direction.

The lamp unit 8 according to the present invention is coupled to the position adjustment unit 6 to emit light forward, thereby providing lighting to a user. Here, a typical lamp unit 8 known in the art may be used without particular limitation as long as it is used for this purpose.

In this case, the lamp unit 8 is coupled to the position adjustment unit 6 and moves in response to the movement of the position adjustment unit 6, which moves by action of the driving unit 4, and a position of the lamp unit 8 is then changed.

According to a specific exemplary embodiment, the lamp unit 8 according to the present invention includes a housing 24 configured to provide an appearance of the lamp unit 8, a body 20 positioned so that grooves can be formed on the inside surface of the housing 24, and a lamp 22 inserted and anchored in the grooves of the body 20.

In this case, the lamp 22 moves back and forth inside the body by the rotation of the body 20 and is configured to change an area exposed to the lamp 22, thereby changing a lighting range of the lamp 22.

By way of example, as shown in FIG. 5, when the body 20 of the lamp unit 8 rotates in one direction, the body 20 moves toward the center of gravity 26 of the position adjustment unit 6 coupled to the driving shaft of the driving unit 4, and an area exposed to light, that is, a size of a spot, is decreased, which makes it possible to illuminate a deep and narrow region more effectively and intensively during surgery of deep and narrow regions. When the body 20 rotates in the opposite direction, the body 20 recedes from the center of gravity 26 of the position adjustment unit 6, and a size of the spot may be increased to illuminate a larger area.

The imaging unit 10 according to the present invention is coupled to one side of the body 2 to take an image of the eye. Here, a typical imaging unit 10 may be used without particular limitation as long as it is used for this purpose.

In this case, a camera, for example, a digital camera or a CCD camera may be used as the imaging unit 10. Here, the imaging unit 10 may be coupled to one side of a guide bar 16 longitudinally extending from one side surface of the body 2 to ensure that the user has a clear line of sight.

Also, the two imaging units 10 may be provided in the vicinity of the left and right eyes, as necessary, so that two images can be taken in both the left and right eyes of the user.

The controller 12 according to the present invention may be coupled to the driving unit 4 and the imaging unit 10 to analyze the image taken by the imaging unit 10, track, and preferably calculate, a position of the eye, activate the driving unit 4 based on the calculated position of the eye, and adjust a direction such that the lamp unit 8 coupled to the position adjustment unit 6 can emit light to correspond to a position of the eye, using the method of tracking a position of an eye according to the present invention.

A typical controller 12 known in the art may be used without limitation as long as it is used for this purpose. Preferably, a printed circuit board may be used as the controller 12.

The power supply unit 14 according to the present invention is coupled to the controller 12, the driving unit 4 and the lamp unit 8 to apply an electric current thereto. Typical power supply units 14 known in the art may be used without limitation as long as they are used for this purpose.

Here, the power supply unit 14 may be coupled to the controller 12, the driving unit 4 and/or the lamp unit 8 by means of an electric wire 18.

According to one specific exemplary embodiment, the power supply unit 14 is positioned independent from the medical head lamp and may apply an electric current to the medical head lamp via an electric wire. However, a rechargeable cell or battery may be coupled to one side of the body 2 of the medical head lamp so that a user can move freely.

Here, when the power supply unit 14 is coupled to one side of the body 2 of the medical head lamp, the power supply unit 14 may be provided in the other side of the body 2 in which the lamp unit 8 is positioned and which faces one side of the body 2.

Furthermore, the power supply unit 14 may also be formed integrally with the controller 12.

The method of tracking a position of an eye according to the present invention can be useful in binarizing an image of an eye region taken by a camera, extracting a feature point form the image, tracking a position of an eye, and controlling a lighting angle of a lamp provided in a head lamp to automatically correspond to the direction of a user's gaze.

While the invention has been shown and described with reference to certain exemplary embodiments thereof, it will be understood by those skilled in the art that various changes in form and details may be made therein without departing from the scope of the invention as defined by the appended claims.

What is claimed is:

1. A method of tracking a position of an eye, comprising:
   i) a binarization step to convert each obtained images of the left and right eye regions of the face into a binary number image;
   ii) a feature point extraction step to classify a corner of the eye, maximum and minimum values of the pupil of the eye, and extracting a feature point from the binary number image on which the binarization step is completed;
   iii) a distance and inclination calculation step to calculate a distance and inclination between the corner and the pupil of the eye using the feature point extracted through the feature point extraction step; and
   iv) an eye gaze direction determination step to determine a gaze direction of the eye based on the distance and inclination calculated through the distance and inclination calculation step,
   wherein the distance and inclination between the corner and the pupil of the eye are calculated according to the following Equations 1 and 2, Distance=(maximum value of pupil+minimum value of pupil)/2−corner of the eye          Equation 1

Inclination=maximum value of pupil−minimum value of the pupil.          Equation 2

2. The method of claim 1, prior to the binarization step of Step i), further comprising:
   a skin color removal operation to remove a skin color from the obtained image.

3. The method of claim 2, wherein the removal of the skin color is performed by binarizing the obtained image only when red, green and blue pixel values in the image satisfy a predetermined range.

4. The method of claim 1, wherein the feature point extraction step of Step ii) comprises:
   translocating a mask from one end to another end of the binarized image with an increase of one pixel;
   storing a summation value at each pixel position upon the translocation;
   regarding a position in a region in which the summation value first becomes significant as the corner of the eye;
   regarding a position in which a difference between mask values summated at regular distances is greatest as a pupil region; and
   searching for the maximum and minimum values at a position of the pupil.

5. A medical head lamp which controls a lighting direction of the medical head lamp using the method of tracking a position of an eye defined in claim 1.

6. The medical head lamp of claim 5, comprising:
a body mounted on the head;
a driving unit coupled to one side of the body to provide a driving force;
a position adjustment unit coupled to one side of the driving unit;
a lamp unit which is coupled to one side of the position adjustment unit, moves in response to the movement of the position adjustment unit, and emits light forward;
an imaging unit coupled to one side of the body to take an image of an eye region;
a controller coupled to the driving unit and the imaging unit to analyze the image taken by the imaging unit, calculate a position of the eye, and activate the driving unit based on the calculated position of the eye; and
a power supply unit coupled to the controller, the driving unit, and the lamp unit to apply an electric current thereto.

7. The medical head lamp of claim 6, wherein the two imaging units are provided in the vicinity of the left and right eyes.

\* \* \* \* \*